United States Patent [19]
Arnett

[11] Patent Number: 5,817,069
[45] Date of Patent: Oct. 6, 1998

[54] VALVE ASSEMBLY

[75] Inventor: Jeffery D. Arnett, Ypsilanti, Mich.

[73] Assignee: Vadus, Inc., Ann Arbor, Mich.

[21] Appl. No.: 608,280

[22] Filed: Feb. 28, 1996

[51] Int. Cl.⁶ .................................................. A61H 5/00
[52] U.S. Cl. ...................... 604/256; 604/246; 251/149.1
[58] Field of Search ............................... 604/30, 33, 164, 604/167, 169, 246, 249, 256, 283, 905; 251/149.1, 149.6

[56] References Cited

U.S. PATENT DOCUMENTS

| | | | |
|---|---|---|---|
| 4,211,741 | 7/1980 | Ostoich | 264/173 |
| 4,254,773 | 3/1981 | Waldbillig | 128/348 |
| 4,391,029 | 7/1983 | Czuba et al. | 29/450 |
| 4,424,833 | 1/1984 | Spector et al. | 137/849 |
| 4,588,398 | 5/1986 | Daugherty et al. | 604/265 |
| 4,661,300 | 4/1987 | Daugherty | 264/40.6 |
| 4,664,657 | 5/1987 | Williamitis et al. | 604/265 |
| 4,683,916 | 8/1987 | Raines | 137/854 |
| 4,713,057 | 12/1987 | Huttner et al. | 604/164 |
| 4,728,322 | 3/1988 | Walker et al. | 604/165 |
| 4,781,703 | 11/1988 | Walker et al. | 604/264 |
| 4,832,696 | 5/1989 | Luther et al. | 604/192 |
| 4,846,805 | 7/1989 | Sitar | 604/165 |
| 4,883,699 | 11/1989 | Aniuk et al. | 428/36.9 |
| 4,917,669 | 4/1990 | Bonaldo | 604/164 |
| 4,944,728 | 7/1990 | Carrell et al. | 604/164 |
| 4,952,207 | 8/1990 | Lemieux | 604/164 |
| 5,000,740 | 3/1991 | Ducharme et al. | 604/162 |
| 5,013,304 | 5/1991 | Russell et al. | 604/167 |
| 5,051,109 | 9/1991 | Simon | 604/263 |
| 5,085,645 | 2/1992 | Purdy et al. | 604/167 |
| 5,088,985 | 2/1992 | Deras | 604/192 |
| 5,088,986 | 2/1992 | Nusbaum | 604/195 |
| 5,088,987 | 2/1992 | Noonan, Jr. | 604/195 |
| 5,088,988 | 2/1992 | Talonn et al. | 604/198 |
| 5,092,845 | 3/1992 | Chang | 604/164 |
| 5,092,853 | 3/1992 | Couvertier, II | 604/195 |
| 5,108,374 | 4/1992 | Lemieux | 604/164 |
| 5,127,905 | 7/1992 | Lemieux | 604/164 |
| 5,135,504 | 8/1992 | McLees | 604/164 |
| 5,171,230 | 12/1992 | Eland et al. | 604/250 |
| 5,183,469 | 2/1993 | Capaccio | 604/192 |
| 5,188,597 | 2/1993 | Sweeney et al. | 604/110 |
| 5,188,607 | 2/1993 | Wu | 604/167 |
| 5,201,713 | 4/1993 | Rosetti | 604/165 |
| 5,215,527 | 6/1993 | Beck et al. | 604/164 |
| 5,215,528 | 6/1993 | Purdy et al. | 604/164 |
| 5,226,899 | 7/1993 | Lee et al. | 604/282 |
| 5,234,416 | 8/1993 | Macaulay et al. | 604/282 |
| 5,240,537 | 8/1993 | Bodicky | 156/244.13 |
| 5,242,393 | 9/1993 | Brimhall et al. | 604/86 |
| 5,250,034 | 10/1993 | Appling et al. | 604/164 |
| 5,250,066 | 10/1993 | Lambert | 606/181 |
| 5,254,107 | 10/1993 | Soltesz | 604/282 |
| 5,261,885 | 11/1993 | Lui | 604/247 |
| 5,267,971 | 12/1993 | Brimhall | 604/177 |
| 5,267,979 | 12/1993 | Appling et al. | 604/247 |
| 5,273,543 | 12/1993 | Bell et al. | 604/110 |
| 5,279,591 | 1/1994 | Simon | 604/263 |
| 5,300,048 | 4/1994 | Drewes, Jr. et al. | 604/280 |
| 5,304,136 | 4/1994 | Erskine et al. | 604/110 |
| 5,304,140 | 4/1994 | Kugo et al. | 604/281 |
| 5,304,144 | 4/1994 | Brimhall | 604/177 |
| 5,304,149 | 4/1994 | Morigi | 604/192 |
| 5,304,155 | 4/1994 | Lui | 604/247 |
| 5,306,253 | 4/1994 | Brimhall | 604/165 |
| 5,308,330 | 5/1994 | Grimard | 604/110 |
| 5,312,361 | 5/1994 | Zadini et al. | 604/165 |
| 5,312,371 | 5/1994 | Dombrowski et al. | 604/198 |
| 5,316,706 | 5/1994 | Muni et al. | 264/25 |

(List continued on next page.)

*Primary Examiner*—Corrine M. McDermott
*Attorney, Agent, or Firm*—Gardner, Carton & Douglas

[57] ABSTRACT

A valve assembly having a body, an end cap, a resilient septum, and an actuator. The body forms a plurality of fluid recesses. The end cap defines a plurality of projections that form channels. The septum is positioned between the body and the end cap. An actuator device is positioned adjacent the septum for moving the septum away from a shoulder defined in the body to allow fluid to pass through the body, actuator, and end cap. The assembly can include a sharp. The sharp extends through the body, the actuator, the septum and the end cap.

7 Claims, 9 Drawing Sheets

U.S. PATENT DOCUMENTS

| | | | |
|---|---|---|---|
| 5,328,473 | 7/1994 | Fayngold et al. | 604/110 |
| 5,334,144 | 8/1994 | Alchas et al. | 604/68 |
| 5,338,310 | 8/1994 | Lewandowski | 604/192 |
| 5,342,309 | 8/1994 | Hausser | 604/110 |
| 5,344,404 | 9/1994 | Benson | 604/110 |
| 5,344,408 | 9/1994 | Partika | 604/192 |
| 5,353,837 | 10/1994 | Raust | 137/614.18 |
| 5,356,390 | 10/1994 | Erskine | 604/164 |
| 5,370,624 | 12/1994 | Edwards et al. | 604/169 |
| 5,376,073 | 12/1994 | Graves et al. | 604/86 |
| 5,380,298 | 1/1995 | Zabetakis et al. | 604/265 |
| 5,380,554 | 1/1995 | Chee et al. | 604/264 |
| 5,385,554 | 1/1995 | Brimhall | 604/168 |
| 5,385,555 | 1/1995 | Hausser | 604/192 |
| 5,390,898 | 2/1995 | Smedley et al. | 251/149.6 |
| 5,395,341 | 3/1995 | Slater | 604/164 |
| 5,397,512 | 3/1995 | Sloane, Jr. et al. | 264/25 |
| 5,405,323 | 4/1995 | Rogers et al. | 604/53 |
| 5,407,431 | 4/1995 | Botich et al. | 604/110 |
| 5,409,461 | 4/1995 | Steinman | 604/110 |
| 5,409,463 | 4/1995 | Thomas et al. | 604/167 |
| 5,409,644 | 4/1995 | Martin et al. | 264/25 |
| 5,411,486 | 5/1995 | Zadini et al. | 604/198 |
| 5,415,184 | 5/1995 | Peck | 128/880 |
| 5,417,668 | 5/1995 | Setzer et al. | 604/263 |
| 5,419,766 | 5/1995 | Chang et al. | 604/110 |
| 5,419,777 | 5/1995 | Hofling | 604/264 |
| 5,423,766 | 6/1995 | Di Cesare | 604/192 |
| 5,423,773 | 6/1995 | Jimenez | 604/282 |
| 5,425,712 | 6/1995 | Goodin | 604/96 |
| 5,425,735 | 6/1995 | Rosen et al. | 606/128 |
| 5,425,903 | 6/1995 | Sloane, Jr. et al. | 264/22 |
| 5,429,613 | 7/1995 | D'Amico | 604/198 |
| 5,429,617 | 7/1995 | Hammersmark et al. | 604/264 |
| 5,435,314 | 7/1995 | Dias | 128/662.06 |
| 5,437,648 | 8/1995 | Graves et al. | 604/263 |
| 5,439,451 | 8/1995 | Collinson et al. | 604/247 |
| 5,441,489 | 8/1995 | Utsumi et al. | 604/280 |
| 5,443,457 | 8/1995 | Ginn et al. | 604/280 |
| 5,445,619 | 8/1995 | Burns | 604/192 |
| 5,445,624 | 8/1995 | Jimenez | 604/280 |
| 5,446,230 | 8/1995 | Travers et al. | 585/748 |
| 5,447,501 | 9/1995 | Karlsson et al. | 604/198 |
| 5,447,503 | 9/1995 | Miller | 604/280 |
| 5,447,724 | 9/1995 | Helmus et al. | 424/426 |
| 5,449,349 | 9/1995 | Sallee et al. | 604/180 |
| 5,453,095 | 9/1995 | Davila et al. | 604/167 |
| 5,453,099 | 9/1995 | Lee et al. | 604/282 |
| 5,456,668 | 10/1995 | Ogle, II | 604/110 |
| 5,456,674 | 10/1995 | Bos et al. | 604/280 |
| 5,458,658 | 10/1995 | Sircom | 604/192 |
| 5,462,533 | 10/1995 | Daugherty | 604/164 |
| 5,464,398 | 11/1995 | Haindl | 604/280 |
| 5,464,399 | 11/1995 | Boettger | 604/283 |
| 5,472,430 | 12/1995 | Vaillancourt et al. | 604/198 |
| 5,474,539 | 12/1995 | Costa et al. | 604/164 |
| 5,478,313 | 12/1995 | White | 604/110 |
| 5,478,328 | 12/1995 | Silverman et al. | 604/272 |
| 5,569,235 | 10/1996 | Ross et al. | 604/403 |
| 5,573,516 | 11/1996 | Tyner | 604/249 |

VALVE ASSEMBLY

BACKGROUND OF THE INVENTION

The present invention is related to a valve assembly. More specifically, the invention is directed to a valve assembly for use in the regulation of fluid flow to and from a blood vessel.

Valve assemblies for various medical uses are known in the art. Examples of such assemblies are disclosed in U.S. Pat. Nos. 4,254,773; 4,683,916; 5,171,230; 5,242,393; and 5,405,323.

It has been found that there is a need for a valve assembly that provides a superior seal within the assembly to prevent leakage. There is also a need for a valve assembly that can be used with a sharp. Examples of sharps include needles and trocars. The present invention satisfies the above-identified needs.

SUMMARY OF THE INVENTION

The present invention is directed to a valve assembly having a body. The body has a first end, a second end, an exterior surface and an interior surface. The interior surface defines a body fluid passageway extending between the first and second ends. The interior surface defines a chamber having a cylindrical side wall adjacent the first end. The cylindrical side wall defines a plurality of fluid recesses. The interior surface defines an annular septum shoulder adjacent the cylindrical side wall.

An end cap is positioned adjacent the first end of the body. The end cap is in communication with the chamber of the body. The end cap has an attachment end, a body end, an outer surface and an inner surface. The inner surface defines an end cap fluid passageway extending between the attachment end and the body end. A catheter or intravenous (IV) luer fitting can be attached to the attachment end. The body end includes a plurality of spaced outwardly extending projections adjacent the end cap fluid passageway. The projections are adjacent the chamber of the body.

The assembly further includes a septum or seal that has a shoulder surface and an opposed projections surface. The septum has a substantially circular chamber wall extending between the shoulder and projections surfaces. The shoulder surface engages the septum shoulder of the body to form a seal when the valve is in a closed position. The projections surface engages the projections. The chamber wall is adjacent the cylindrical side wall of the chamber. The chamber wall and the fluid recesses form a plurality of chamber fluid passageways.

An actuator is positioned in the body fluid passageway adjacent the second end of the body. The actuator moves the shoulder surface of the septum away from the septum shoulder of the body to allow fluid to flow through the body fluid passageway, the chamber fluid passageways and the end cap fluid passageway.

The assembly can include a sharp, such as a needle, having a first needle end, a second needle end, a needle exterior surface and a needle interior surface. The needle interior surface defines a needle fluid passageway extending between the first needle end and the second needle end. The needle extends through the actuator, the septum and the end cap fluid passageway. If a catheter is attached to the attachment end of the end cap, the needle extends through the catheter fluid passageway.

It is the primary object of the present invention to provide a valve assembly that has a superior seal within the assembly for preventing leakage of fluid.

It is an important object of the present invention to provide a valve assembly that can be used with a sharp.

Other objects and advantages of the present invention shall become apparent to those skilled in the art upon a review of the following detailed description of the preferred embodiments and the accompanying drawings.

DETAILED DESCRIPTION OF THE PREFERRED EMBODIMENTS

Figure 1:
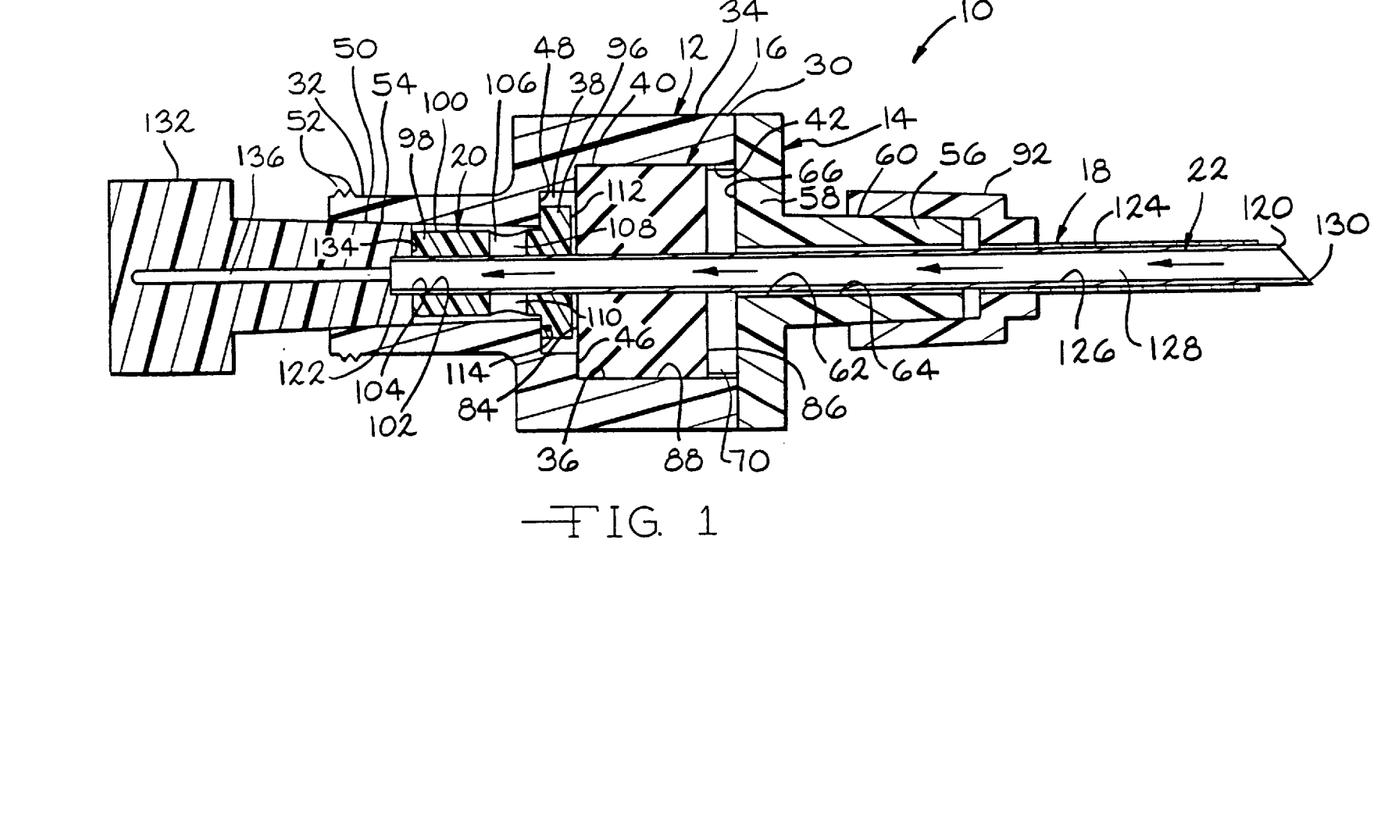
FIG. 1 is a cross-sectional view taken through the center of a first embodiment valve assembly according to the present invention including a needle and a catheter.
Figure 2:
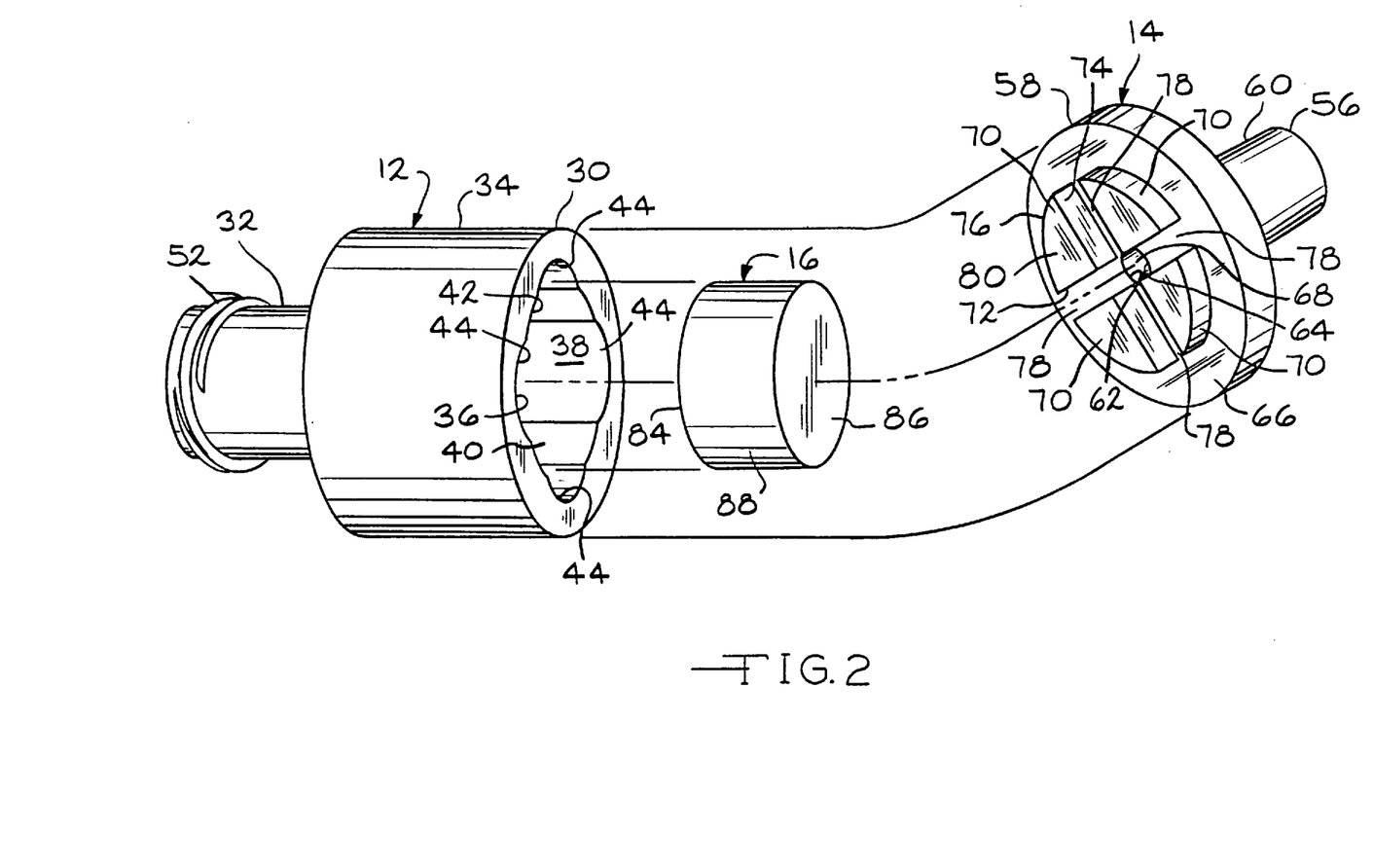
FIG. 2 is an exploded view showing the body, septum and end cap of the present invention.
Figure 5:
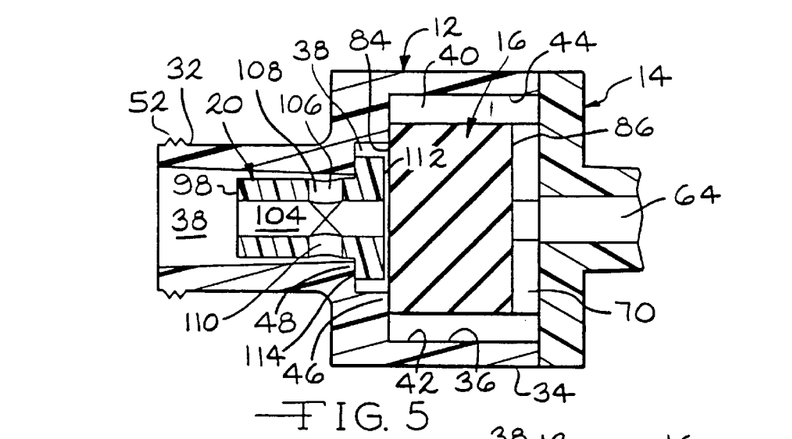
FIG. 5 is a cross-sectional view taken along line 5—5 of FIG. 7 showing the assembly in a sealed position.
Figure 7:
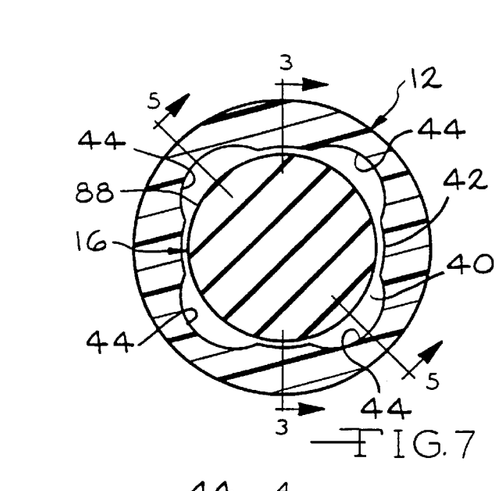
FIG. 7 is a cross-sectional view taken along line 7—7 of FIG. 3.

The preferred embodiments and best mode of the present invention shall now be described in detail with reference being made to the accompanying drawings. The valve assembly of the present invention is indicated generally in the drawings by the reference number "10". As shown in FIG. 1, the assembly 10 includes a body 12, an end cap 14, a septum 16 and an actuator 20. Depending on the use of the present invention, the assembly 10 can also include a catheter 18 and a sharp, such as a needle 22. Referring to FIGS. 1 and 2, the body 12 has a first end 30, a second end 32, an exterior surface 34 and an interior surface 36. The interior surface 36 defines a body fluid passageway 38 extending between the first and second ends 30 and 32. The interior surface 36 defines a chamber 40 having a cylindrical side wall 42 adjacent the first end 30. As shown in FIGS. 2, 5 and 7, the cylindrical side wall 42 defines a plurality of fluid recesses 44. In the present embodiment, there are four fluid recesses 44 defined by the cylindrical side wall 42. It should be understood that any number of fluid recesses 44 can be defined by the side wall 42. As shown in FIG. 1, the interior surface 36 defines an annular septum shoulder 46 adjacent the chamber 40 of the body 12. The interior surface 36 further defines an annular actuator shoulder 48 adjacent the septum shoulder 46 in the body fluid passageway 38.

Figure 4:
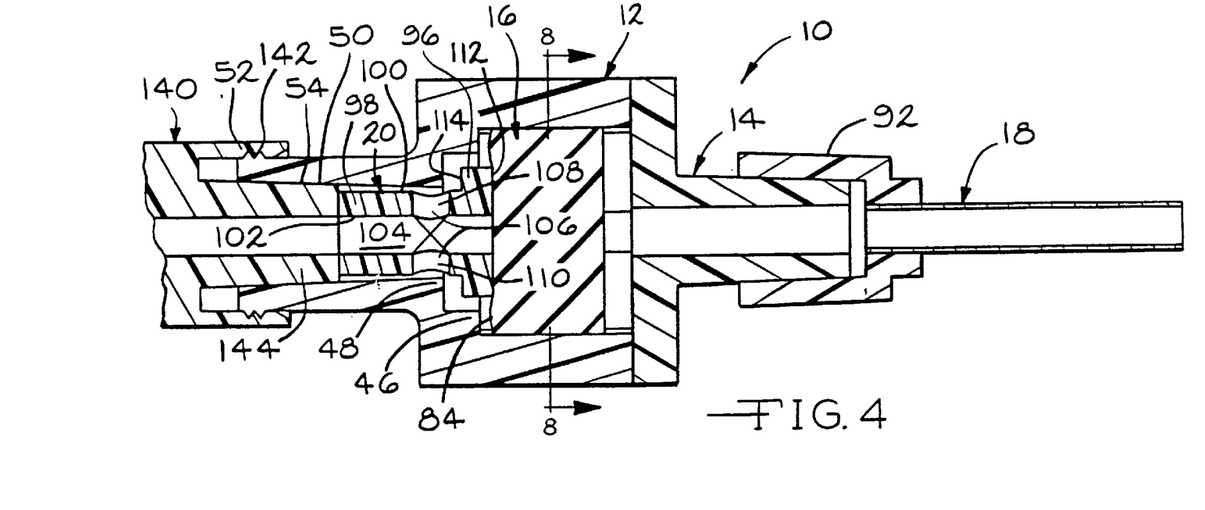
FIG. 4 is a cross-sectional view taken along line 4—4 of FIG. 8 showing the assembly in an open position.

Referring now to FIGS. 1, 2 and 4, the exterior surface 34 of the body 12 includes a luer attachment fitting 50. The luer attachment fitting 50 includes luer attachment members 52 and a luer tapered fitting 54. The luer attachment fitting 50 is positioned on the second end 32 of the body 12. The luer attachment fitting 50 can be the type set forth in American National Standard Institute No. ANSI\HIMA MD70.1—1983.

As shown in FIGS. 1 and 2, the end cap 14 is positioned adjacent the first end 30 of the body 12. The end cap 14 is in communication with the chamber 40 of the body 12. The end cap 14 has an attachment end 56, a body end 58, an outer surface 60 and an inner surface 62. The inner surface 62 defines an end cap fluid passageway 64 that extends between the attachment end 56 and the body end 58.

Figures 6, 8:
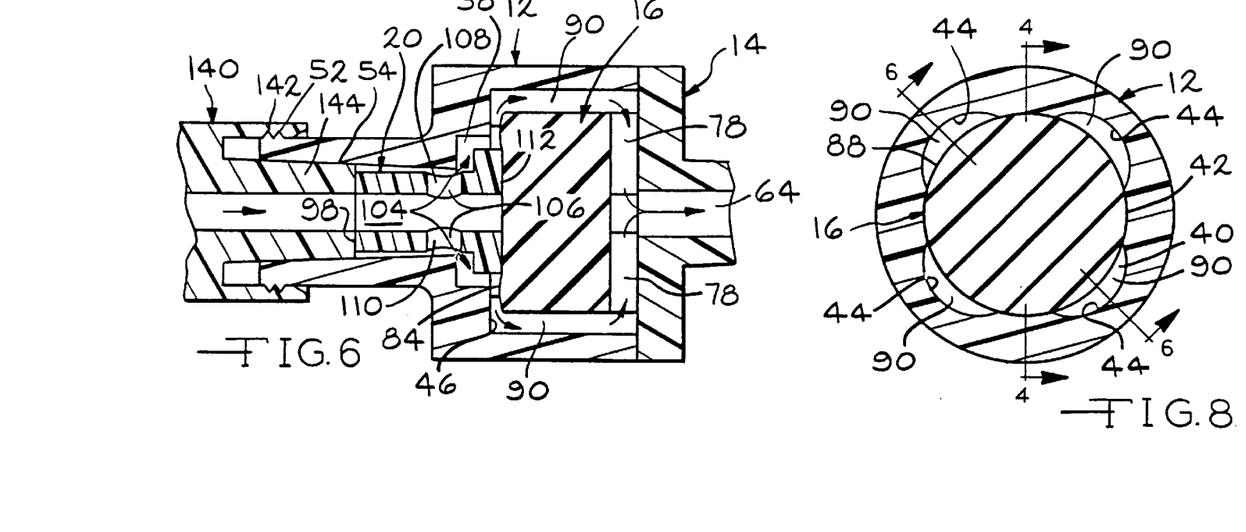
FIG. 6 is a cross-sectional view taken along line 6—6 of FIG. 8 showing the assembly in an open position.
FIG. 8 is a cross-sectional view taken along line 8—8 of FIG. 4.

Referring to FIG. 2, the body end 58 of the end cap 14 includes an annular face 66. The opening 68 of the end cap fluid passageway 64 is positioned in the center of the annular face 66. A plurality of spaced outwardly extending projections 70 are positioned on the annular face 66. In the present embodiment, there are four projections 70. Each of the projections 70 is in the shape of a sector having first and second equidistant sides 72 and 74, and an arc 76. The arcs 76 of the projections 70 generally define a circle with the center of the circle being the opening 68. The projections 70 encompass the opening 68. As shown in FIG. 2, the projections 70 define a plurality of channels 78. In the present embodiment, four channels 78 are defined by the four projections 70. As described below, the channels 78 are used to channel fluid to the opening 68. As shown in FIGS. 1, 2 and 6, the projections 70 are positioned in the chamber 40 adjacent the cylindrical side wall 42 of the body 12. The projections 70 are positioned so that the channels 78 are in communication with the fluid recesses 44. As shown in FIG. 2, each of the projections 70 includes a flat septum surface 80.

Referring now to FIGS. 1, 2, 7 and 8, the septum 16 has a shoulder surface 84 and an opposed projections surface 86. A circular chamber wall 88 extends between the shoulder and projections surfaces 84 and 86. The shoulder surface 84 engages the septum shoulder 46 defined by the body 12 to form a seal when the assembly 10 is in a sealed position. The projections surface 86 engages the septum surfaces 80 of the projections 70. The septum surfaces 80 provide flat surfaces upon which the septum 16 can be seated.

As shown in FIGS. 7 and 8, the chamber wall 88 of the septum 16 is positioned adjacent the cylindrical side wall 42 and fluid recesses 44 of the chamber 40. When so positioned, the chamber wall 88 and the fluid recesses 44 form a plurality of chamber fluid passageways 90. In the present embodiment, four chamber fluid passageways 90 are formed.

The septum 16 is made of a resilient, compressible elastomeric material. The septum 16 should be made of a material that can be compressed or deformed numerous times without losing its original shape. The material used should also allow the septum 16 to be pierced by a sharp, such as a needle 22, as described below, and be self-sealing after removal of the sharp. An example of a material that can be used to make the septum 16 is a biocompatible synthetic polymer material.

Figure 3:
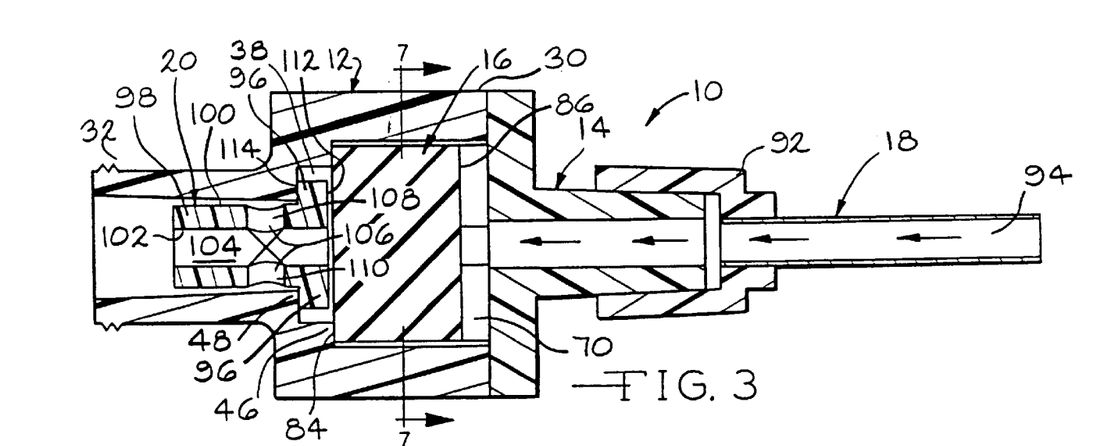
FIG. 3 is a cross-sectional view taken along line 3—3 of FIG. 7 showing the assembly according to the present invention in a sealed position.

As shown in FIG. 1, the catheter 18 is positioned on the attachment end 56 of the end cap 14 by a catheter fitting 92. The catheter fitting 92 can be the type set forth in American National Standard Institute No. ANSI/HIMA MD70.1—1983. The catheter 18 can also be directly attached to the end cap 14 (not shown). As shown in FIG. 3, a catheter fluid passageway 94 extends through the catheter 18.

Referring to FIGS. 1, 3 and 4, the actuator 20 includes a first actuator end 96, a second actuator end 98, an exterior actuator surface 100 and an interior actuator surface 102. The interior actuator surface 102 defines an actuator fluid passageway 104 extending between the first actuator end 96 and the second actuator end 98. The actuator 20 further includes a second fluid passageway 106 that extends perpendicular to the first actuator fluid passageway 104. The second actuator fluid passageway 106 consists of openings 108 and 110 that each extends from the interior actuator surface 102 to the exterior actuator surface 100. As shown in FIGS. 3 and 4, the actuator exterior surface 100 defines an annular septum contact surface 112 and an opposed actuator shoulder contact surface 114. The septum contact surface 112 engages the shoulder surface 84 of the septum 16. The actuator shoulder contact surface 114 engages the actuator shoulder 48 of the body 12. The actuator 20 is positioned in the body fluid passageway 38 adjacent the second end 32 of the body 12.

Referring to FIG. 1, the needle 22 includes a first needle end 120, a second needle end 122, a needle exterior surface 124 and a needle interior surface 126. The needle interior surface 126 defines a needle fluid passageway 128 extending between the first needle end 120 and the second needle end 122. The needle 22 includes a sharp point 130 at the first needle end 120. During the manufacture of the assembly 10, the point 130 pierces the septum 16 to allow the needle 22 to be inserted through the septum. When the assembly 10 is used, the point 130 is used to pierce the skin and blood vessel of a patient. A handle 132 is positioned adjacent the second needle end 122. The handle 132 includes an actuator end 134 adjacent the second actuator end 98 of the actuator 20. The handle 132 includes an indicator channel 136 that is in communication with the needle fluid passageway 128. The handle 132 can be made of a transparent material, such as clear plastic. The handle 132 is transparent so that one using the assembly 10 can readily see blood or other fluid once the needle 22 is properly inserted. As shown in FIG. 1, the needle 22 extends through the actuator fluid passageway 104, the septum 16, the end cap fluid passageway 64 and the catheter fluid passageway 94.

The use of the assembly 10 of the present invention will now be described. Referring to FIGS. 1 and 3 through 8, one using the assembly 10 locates a blood vessel on a patient's body. The point 130 of the needle 22 and the catheter 18 are inserted through the skin and blood vessel of the patient. Once the needle 22 is in the blood vessel, blood "flashes" through the needle fluid passageway 128, in the direction shown by the arrows in FIG. 1, to the indicator channel 136 of the handle 132. Once blood is seen in the indicator channel 136, the needle 22 is removed from the assembly 10 by pulling the handle 132 away from the second end 32 of the body 12. In so doing, the needle 22 is removed from the catheter fluid passageway 94, the end cap fluid passageway 64, the septum 16, the actuator fluid passageway 104 and the body fluid passageway 38. The needle 22 is then discarded. After removal of the needle 22 from the blood vessel, the catheter 18 remains positioned in the blood vessel.

Referring to FIGS. 3 and 5, a seal is formed between the septum shoulder 46 of the body 12 and the shoulder surface 84 of the septum 16. The seal is tight because the shoulder surface 84 of the septum 16 is forced against the septum shoulder 46 due to the resilient nature of the septum and the contact of the projections surface 86 against the projections 70. Therefore, any blood flowing in the direction of the arrows shown in FIG. 3 will be prevented by the seal from escaping into the body fluid passageway 38 of the body 12. This prevents blood from exiting the second end 32 of the body 12.

Referring to FIGS. 4, 6 and 8, a male luer 140, which is attached to intravenous tubing or other apparatus (not shown), can be attached to the second end 32 of the body 12. The luer 140 mates with the luer attachment fitting 50 by rotating the luer tapered fitting 54 into the luer 140 until recesses 142 engage the luer attachment projections 52. The luer 140 includes a male member 144 that is inserted in the body fluid passageway 38. The male member 144 engages the second actuator end 98 of the actuator 20. The engagement of the male member 144 with the second actuator end 98 causes the septum contact surface 112 of the actuator 20 to engage and press against the shoulder surface 84 of the septum 16. Due to the resilient nature of the septum 82, the shoulder surface 84 becomes disengaged from the septum shoulder 46 of the body 12. This breaks the seal between the shoulder surface 84 and the septum shoulder 46. As shown by the arrows in FIG. 6, fluid is free to flow from the luer 140 through the first actuator fluid passageway 104 to the openings 108 and 110 of the second actuator fluid passageway 106 through the chamber fluid passageways 90 to the channels 78 through the end cap fluid passageway 64 and to the catheter fluid passageway 94 into the blood vessel. Fluid can also flow in the opposite direction. The assembly 10 can be resealed by removing the luer 140 from the second end 32 of the body 12 thereby causing the septum 16 to regain its original shape to form a seal between the shoulder surface 84 and the septum shoulder 46. Upon removal of the luer 140, the axial movement of the actuator 20 is restricted when the shoulder contact surface 114 engages the actuator shoulder 48 of the body 12.

The description of the assembly 10 has included a catheter 18 and a needle 22. It should be understood that the present invention can also be used as a valve in a needleless access system. In this type of system, the attachment end 56 of the end cap 14 could include a luer attachment fitting of the type set forth in American National Standard Institute No. ANSI/ HIMA MD70.1—1983. This would allow the attachment end 56 to mate with a luer in communication with, for example, IV tubing. The second end 32 of the body 12 includes a luer attachment fitting 50, as previously described, so that a luer 140 in communication with, for example, IV tubing can be attached to the body 12. When the valve assembly 10 is used in a needleless access system, fluid is free to flow from the luer 140 through the first actuator fluid passageway 104 to the openings 108 and 110 of the second actuator fluid passageway 106 through the chamber fluid passageways 90 to the channels 78 through the end cap fluid passageway 64 and to the luer attached to the attachment end 56 of the end cap 14. The assembly 10 can be resealed by removing the luer 140 from the body 12. This would cause the septum 16 to engage the septum shoulder 46 as previously described to seal the assembly 10.

Figure 9:
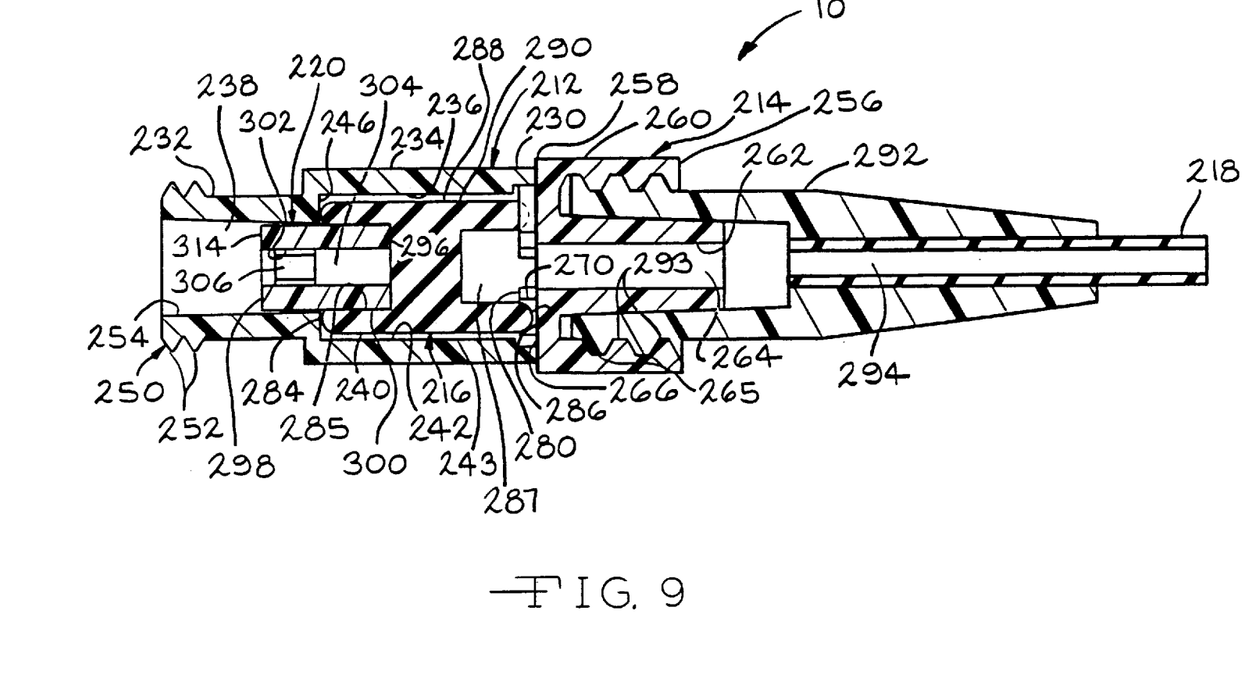
FIG. 9 is a cross-sectional view taken through the center of a second embodiment of the valve assembly according to the present invention including a catheter.
Figure 10:
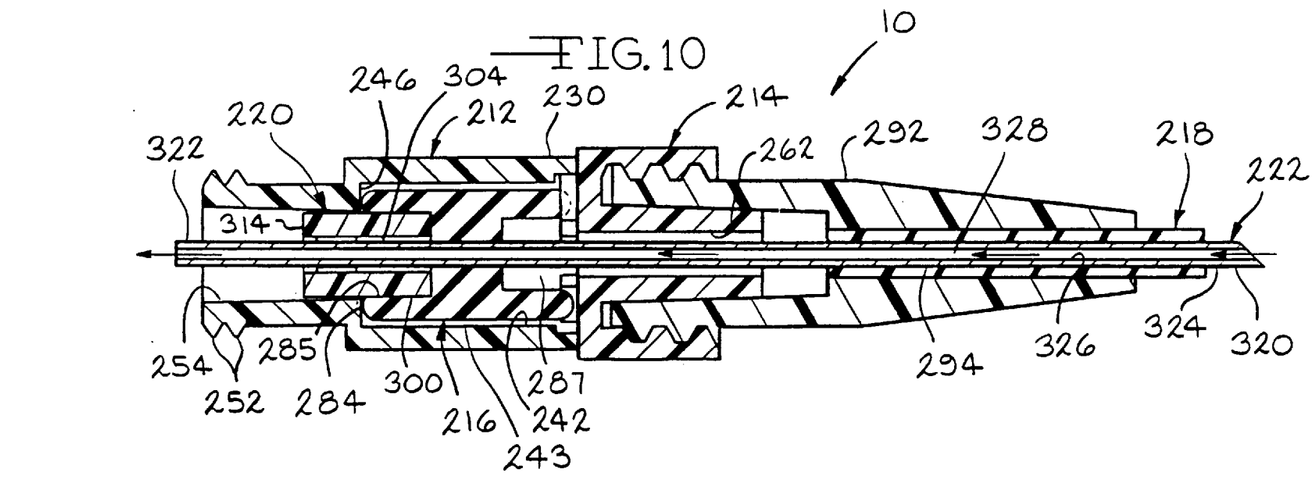
FIG. 10 is a view similar to the view of FIG. 9 further including a needle.
Figure 11:
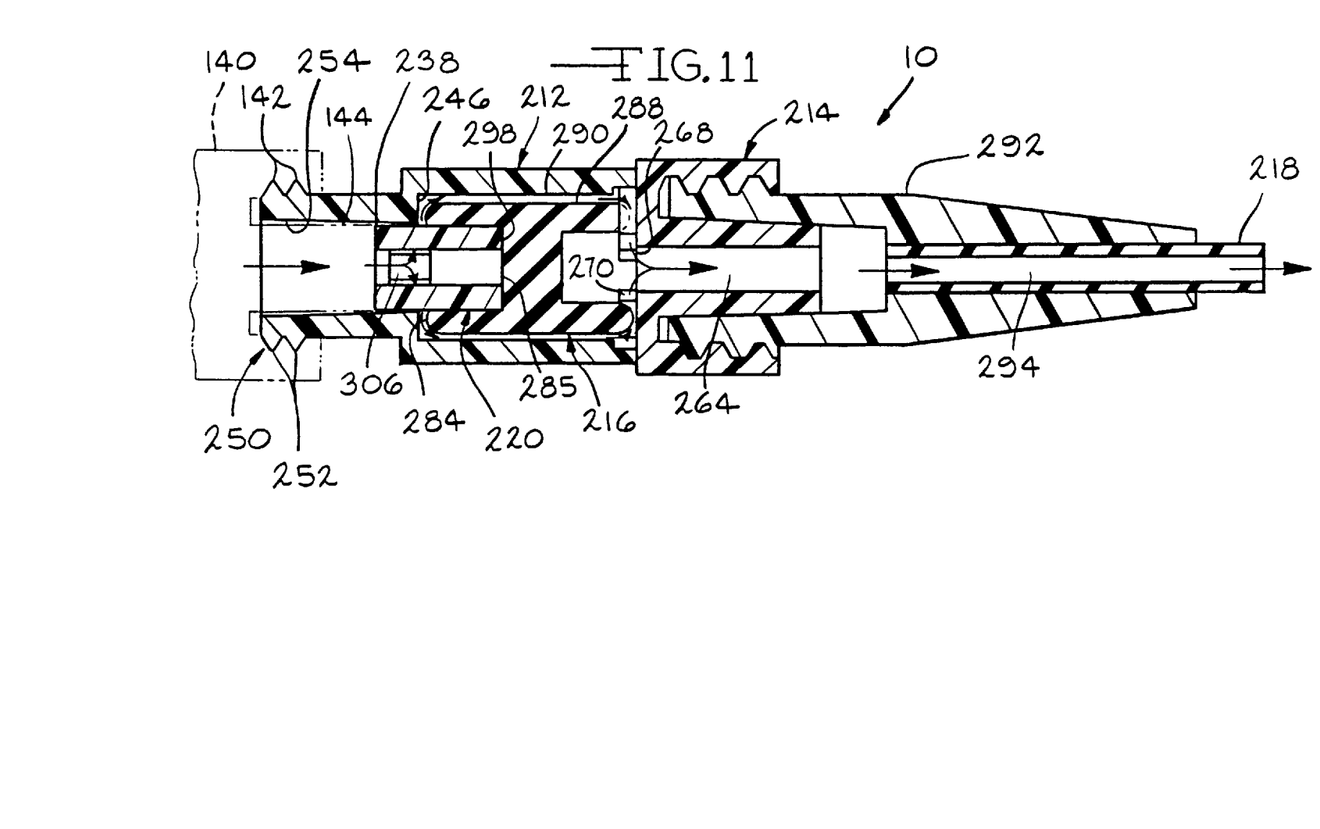
FIG. 11 is a view similar to the view of FIG. 9 showing the assembly in an open position.

A second embodiment of the valve assembly 10 of the present invention is shown in FIGS. 9 through 15. Referring to FIGS. 9 through 11, the second embodiment assembly 10 includes a body 212, an end cap 214, a septum 216 and an actuator 220. As shown in FIG. 10, the assembly 10 can also include a catheter 218 and a sharp, such as a needle 222. It should be understood that the assembly 10 can be used as a valve in a needleless access system without a catheter 218 or needle 222 as previously described.

Figure 13:
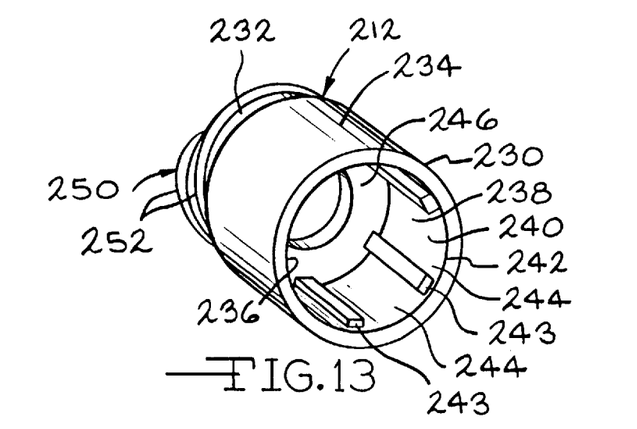
FIG. 13 is a perspective view of a second embodiment body.

Referring to FIGS. 9 and 13, the body 212 has a first end 230, a second end 232, an exterior surface 234 and an interior surface 236. The interior surface 236 defines a body fluid passageway 238 extending between the first and second ends 230 and 232. The interior surface 236 defines a chamber 240 having a cylindrical side wall 242 adjacent the first end 230. As shown in FIG. 13, the cylindrical side wall 242 defines a plurality of longitudinally extending chamber members 243 that define a plurality of fluid recesses 244. In the second embodiment, there are six chamber members 243 that define six fluid recesses 244. It should be understood that any number of fluid recesses 244 can be defined by the chamber members 243. As shown in FIGS. 9 and 13, the interior surface 236 defines an annular septum shoulder 246 adjacent the chamber 240 of the body 212.

Still referring to FIGS. 9 and 13, the exterior surface 234 of the body 212 includes a luer attachment fitting 250. The luer attachment fitting 250 includes luer attachment members 252 and a luer tapered fitting 254. The luer attachment fitting 250 is positioned on the second end 232 of the body 212.

Figure 14:
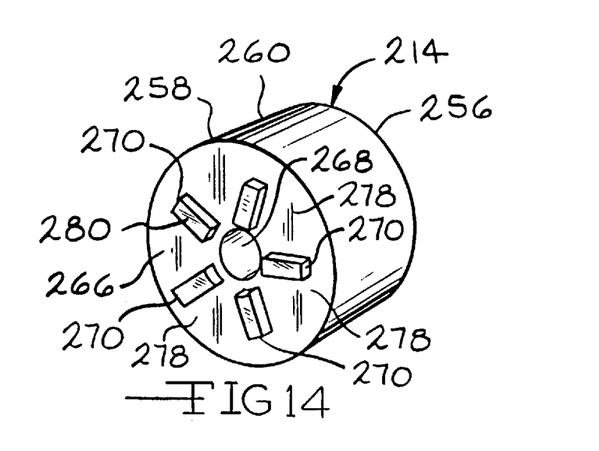
FIG. 14 is a perspective view of a second embodiment end cap.

Referring to FIGS. 9 and 14, the end cap 214 is positioned adjacent the first end 230 of the body 212. The end cap 214 is in communication with the chamber 240 of the body 212. The end cap 214 has an attachment end 256, a body end 258, an outer surface 260 and an inner surface 262. The inner surface 262 defines an end cap fluid passageway 264 that extends between the attachment end 256 and the body end 258. As shown in FIG. 9, the attachment end 256 can include a plurality of threads 265 for receiving the catheter 218. It should be understood that the attachment end 256 can include a variety of attachment devices or fittings depending on the use of the assembly 10. For example, the attachment end 256 can include a luer attachment fitting for mating engagement with a luer.

As shown in FIG. 14, the body end 258 of the end cap 214 includes an annular face 266. The opening 268 of the end cap fluid passageway 264 is positioned in the center of the annular face 266. A plurality of spaced outwardly extending end cap projections 270 are positioned on the annular face 266. In the present embodiment, there are five end cap projections 270. The end cap projections 270 encompass the opening 268. The end cap projections 270 define a plurality of channels 278. In the present embodiment, five channels 278 are defined by the five end cap projections 270. The channels 278 are used to channel fluid to the opening 268. As shown in FIG. 9, the end cap projections 270 are positioned in the chamber 240 adjacent the cylindrical side wall 242 of the body 212. The end cap projections 270 are positioned so that the channels 278 are in communication with the fluid recesses 244. As shown in FIG. 14, each of the end cap projections 270 includes a flat septum surface 280.

As shown in FIG. 9, the septum 216 has a shoulder surface 284 that defines an actuator recess 285. The septum 216 further includes a projections surface 286 that defines an end cap recess 287. A circular chamber wall 288 extends between the shoulder and projections surfaces 284 and 286. The shoulder surface 284 engages the septum shoulder 246 defined by the body 212 to form a seal when the assembly 10 is in a sealed position. The projections surface 286 engages the septum surfaces 280 of the projections 270. The septum 216 is pre-loaded in the chamber 240 in order to properly seat the septum in the assembly 10. As shown in FIG. 9, the positive pressure resulting from the pre-loading causes portions of the projections surface 286 of the septum 216 to extend beyond the septum surfaces 280 of end projections 270. The extending portions of the projections surface 286 do not contact the annular face 266 of the end cap 214 to interfere with the flow of fluid through the assembly 10.

As shown in FIGS. 9 and 11, the chamber wall 288 of the septum 216 is positioned adjacent the cylindrical side wall 242 and fluid recesses 244 of the chamber 240. When so positioned, the chamber wall 288 and the fluid recesses 244 form a plurality of chamber fluid passageways 290. In the present embodiment, six chamber fluid passageways 290 are formed.

Referring to FIG. 9, the septum 216 is made of a resilient, compressible elastomeric material. The septum 216 should be made of a material that can be compressed or deformed numerous times without losing its original shape. The material used should also allow the septum 216 to be pierced by a sharp, such as a needle 222, and be self-sealing after removal of the sharp. As previously described, an example of a material that can be used to make the septum 216 is a biocompatible synthetic polymer material.

Referring to FIG. 9, the catheter 218 is positioned on the attachment end 256 of the end cap 214 by a catheter fitting 292. The catheter fitting 292 includes a plurality of threads 293 that mate with the threads 265 of the end cap 214. The catheter 218 includes a catheter fluid passageway 294.

Figure 12:
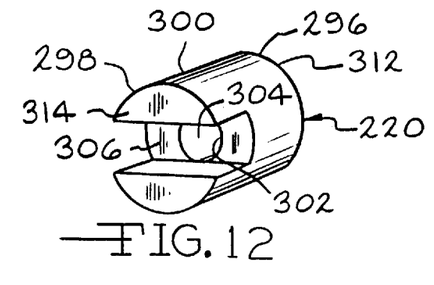
FIG. 12 is a perspective view of a second embodiment actuator.

Referring to FIGS. 9 and 12, the actuator 220 includes a first actuator end 296, a second actuator end 298, an exterior actuator surface 300, and an interior actuator surface 302. The interior actuator surface 302 defines a needle passageway 304 extending between the first actuator end 296 and the second actuator end 298. The interior actuator surface 302 defines a fluid passageway 306 adjacent the second actuator end 298. As shown in FIGS. 9 and 12, the actuator exterior surface 300 defines an annular septum contact surface 312 and an opposed fitting contact surface 314. A portion of the exterior surface 300 and the septum contact surface 312 engage the actuator recess 285 of the septum 216. As shown in FIG. 11, the fitting contact surface 314 engages, for example, the male member 144 of a luer 140. The actuator 220 is positioned in the body fluid passageway 238 adjacent the second end 232 of the body 212.

Referring to FIG. 10, the needle 222 includes a first needle end 320, a second needle end 322, a needle exterior surface 324 and a needle interior surface 326. The needle interior surface 326 defines a needle fluid passageway 328 extending between the first needle end 320 and the second needle end 322. As shown in FIG. 10, the needle 322 extends through the needle passageway 304 of the actuator 220, the septum 216, the end cap fluid passageway 264 and the catheter fluid passageway 294.

Figure 15:
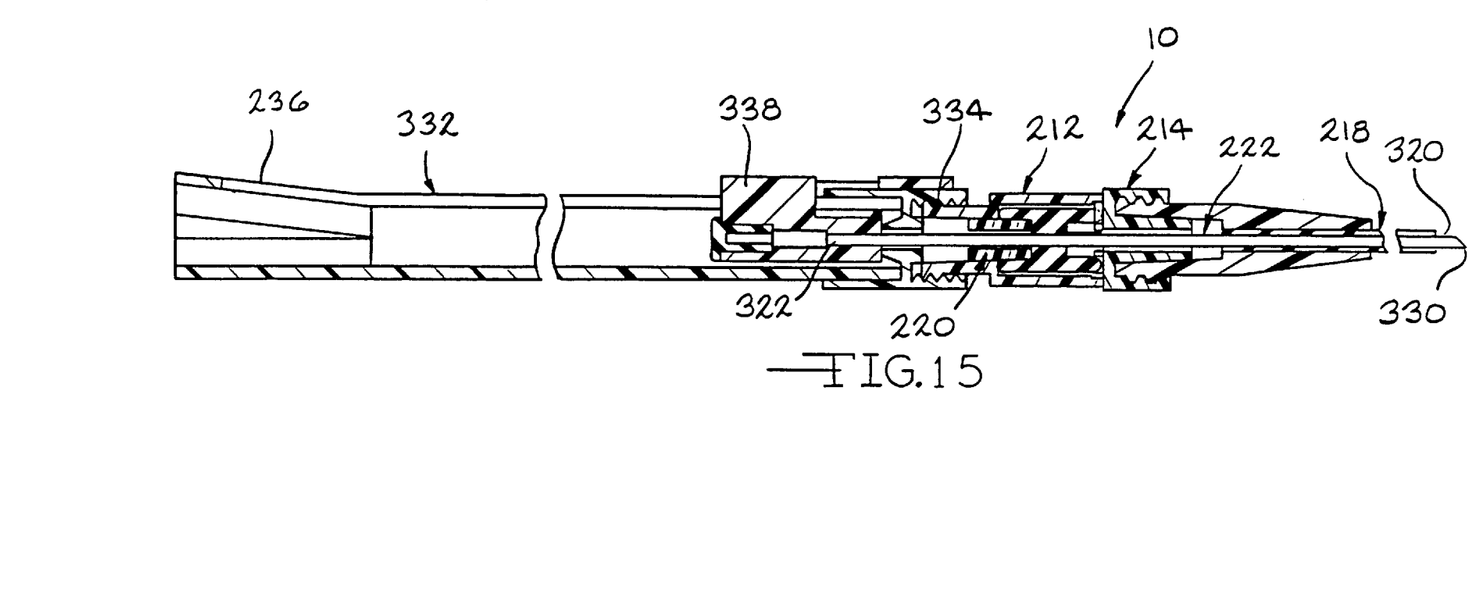
FIG. 15 is a cross-sectional view taken through the center of the second embodiment assembly including a needle, needle guard assembly and catheter.

Referring to FIG. 15, an embodiment of a combined needle handle and guard 332 is shown. The handle 332 includes a first handle end 334 and a second handle end 336. The first end 334 is attached to the second end 232 of the body 212. The second needle end 322 of the needle 222 is attached to a reciprocating handle member 338. When the needle 222 is to be removed from the assembly 10, the handle member 338 is moved from the first end 334 of the handle 332 toward the second end 336. When the handle member 338 is adjacent the second end 336, the needle 222, including the sharp point 330, is completely retracted into the body of the handle 332. The handle 332 can then be removed from the assembly 10 and discarded. Once the handle 332 is removed, the second end 232 of the body 212 can receive, for example, a luer.

The use of the second embodiment assembly 10 of the present invention will now be described. Referring to FIGS. 10 and 15, one using the assembly 10 locates a blood vessel on the patient's body. The point 330 of the needle 222 and the catheter 218 are inserted through the skin and blood vessel of the patient. Once the needle 222 is in the blood vessel, blood "flashes" through the needle fluid passageway 328, in the direction shown by the arrows in FIG. 10. The needle 222 is removed from the assembly 10 by pulling the handle member 338 toward the second end 336 of the handle 332. This causes the needle 222 to be removed from the catheter fluid passageway 294, the end cap fluid passageway 264, the septum 216, the needle passageway 304 and the body fluid passageway 238. The handle 332 is then removed from the body 212 and discarded. After removal of the needle 222 from the blood vessel, the catheter 218 remains positioned in the blood vessel.

Referring to FIG. 9, a seal is formed between the septum shoulder 246 of the body 212 and the shoulder surface 284 of the septum 216. Therefore, blood will be prevented by the seal from escaping into the body fluid passageway 238 of the body 212. This prevents blood from exiting the second end 232 of the body 212.

Referring to FIG. 11, a male luer 140 can be attached to second end 232 of the body 212. The luer 140 mates with the luer attachment fitting 250 by rotating the luer tapered fitting 254 into the luer 140 until recesses 142 engage the luer attachment projections 252. The luer 140 includes a male member 144 that is inserted in the body fluid passageway 238. The male member 144 engages the second actuator end 298 of the actuator 220. The engagement of the male member 144 with the second actuator end 298 causes the septum contact surface 312 of the actuator 220 to engage and press against the actuator recess 285 of the resilient septum 216. This causes the shoulder surface 284 to be disengaged from the septum shoulder 246 of the body 212. This breaks the seal between the shoulder surface 284 and the septum shoulder 246. As shown in FIG. 11, fluid is free to flow from the luer 140 through the fluid passageway 306 of the actuator 220 to the chamber fluid passageways 290 to the channels 278 through the end cap fluid passageway 264 and to the catheter fluid passageway 294 into the blood vessel. The assembly 10 can be resealed by removing the luer 140 from the second end 232 of the body 212 thereby causing the septum 216 to regain its original shape to form a seal between the shoulder surface 284 and the septum shoulder 246.

While the invention has been described with reference to preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof. Therefore, it is intended that the invention not be limited to the particular embodiments disclosed as the best mode contemplated for carrying out this invention, but that the invention will include all embodiments falling within the scope of the claims.

I claim:

1. A valve assembly comprising:
    a body having a first end and a second end, said body defining a passageway extending between said first and second ends, said body defining a sealing surface in said passageway;

a resilient septum positioned in said passageway in sealing engagement with said sealing surface, said septum having a substantially solid cylindrical shape;

means for disengaging said septum from said sealing surface to allow fluid flow through said passageway.

2. The valve assembly of claim 1, wherein said septum is self-sealing upon insertion and withdrawal of a needle therethrough.

3. The valve assembly of claim 1, wherein said septum is substantially solid in form.

4. A valve assembly comprising:

a body having a first end, a second end, an exterior surface, and an interior surface, said interior surface defining a substantially cylindrical side wall extending between said first and second ends and a substantially annular septum shoulder adjacent said second end, said cylindrical side wall having a plurality of fluid recesses;

an end cap adjacent said first end of said body, said end cap having an attachment end, a body end, an outer surface and an inner surface, said body end including a plurality of outwardly extending projections;

a resilient septum having a substantially solid cylindrical shape, a shoulder surface, an opposed projections surface, and a substantially circular chamber wall extending between said shoulder and projection surfaces, said shoulder surface engaging said septum shoulder to form a seal, said projections surface engaging said projections to form an end cap fluid passageway, said chamber wall together with said cylindrical side wall forming a plurality of chamber fluid passageways, said chamber fluid passageways being in communication with said end cap passageway;

actuator means positioned in said body fluid passageway adjacent said second end of said body for moving said shoulder surface of said septum away from said shoulder to allow fluid to flow through said chamber and end cap fluid passageways.

5. The valve assembly of claim 4, wherein said exterior surface of said body defines attachment means adjacent said second end.

6. The valve assembly of claim 4, wherein said interior surface of said body defines a substantially annular actuator shoulder in said body fluid passageway, said actuator shoulder being shaped to retain said actuator means within said body.

7. The valve assembly of claim 6, wherein said actuator means is comprised of an actuator body having a first actuator end, a second actuator end, an exterior actuator surface and an interior actuator surface, said interior actuator surface defining an actuator fluid passageway extending between said first actuator end and said second actuator end, said actuator exterior surface defining an annular septum contact surface and an opposed actuator shoulder contact surface, said septum contact surface engaging said septum, and said actuator shoulder contact surface engaging said actuator shoulder.

* * * * *